United States Patent [19]

Sakai et al.

[11] Patent Number: 4,961,833
[45] Date of Patent: Oct. 9, 1990

[54] FIELD-EFFECT TRANSISTOR-TYPE SEMICONDUCTOR SENSOR

[75] Inventors: Tadashi Sakai, Kanagawa; Shigeki Uno, Tokyo; Masao Koyama; Nanao Nakamura, both of Kanagawa, all of Japan

[73] Assignee: Kabushiki Kaisha Toshiba, Kawasaki, Japan

[21] Appl. No.: 327,817

[22] Filed: Mar. 23, 1989

[30] Foreign Application Priority Data

Mar. 31, 1988 [JP] Japan ................................. 63-78715

[51] Int. Cl.$^5$ .................... G01N 27/30; G01N 27/327
[52] U.S. Cl. .................................... 204/403; 204/408; 204/412; 204/415; 204/416; 357/25; 435/291; 435/817
[58] Field of Search .................. 357/25; 204/416, 403, 204/415, 408, 412; 435/291, 817

[56] References Cited

U.S. PATENT DOCUMENTS

| 4,020,830 | 5/1977 | Johnson et al. | 128/635 |
| 4,505,799 | 3/1985 | Baxter | 204/416 |
| 4,791,465 | 12/1988 | Sakai et al. | 357/25 |

FOREIGN PATENT DOCUMENTS 60-47952  3/1985  Japan .

OTHER PUBLICATIONS

Proc. 4th Int. Conf. Solid State Sensors and Actuators, pp. 726-729; H. H. van den Vlekkert et al, "A pH-ISFET and an Integrated pH-Pressure Sensor With Back-Side Contacts"(1987).

*Primary Examiner*—G. L. Kaplan
*Attorney, Agent, or Firm*—Oblon, Spivak, McClelland, Maier & Neustadt

[57] ABSTRACT

A field-effect transistor-type semiconductor sensor is provided which comprises first and second semiconductor substrates bonded strongly to each other interposing a silicon oxide film therebetween by the use of a direct-bonding technique. The first semiconductor substrate is formed into an island-shape, and incorporates a source region, a drain region and a gate region. The island-shaped substrate constitutes an ion-sensitive portion, and is immersed in a solution when in use. The second semiconductor substrate has openings in which source and drain electrodes are formed.

30 Claims, 6 Drawing Sheets

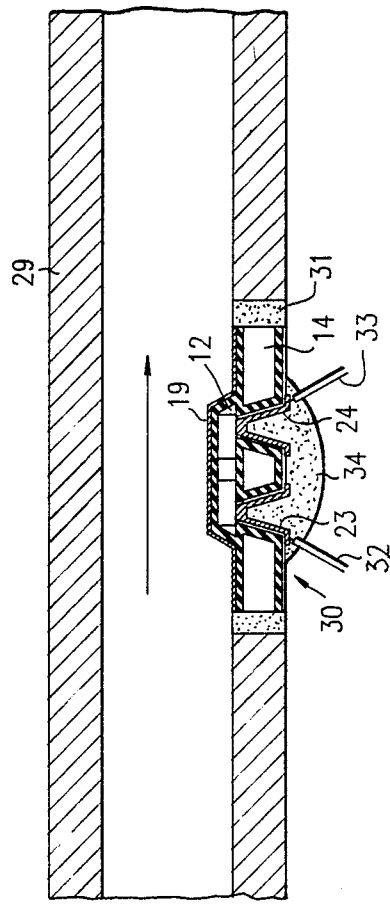
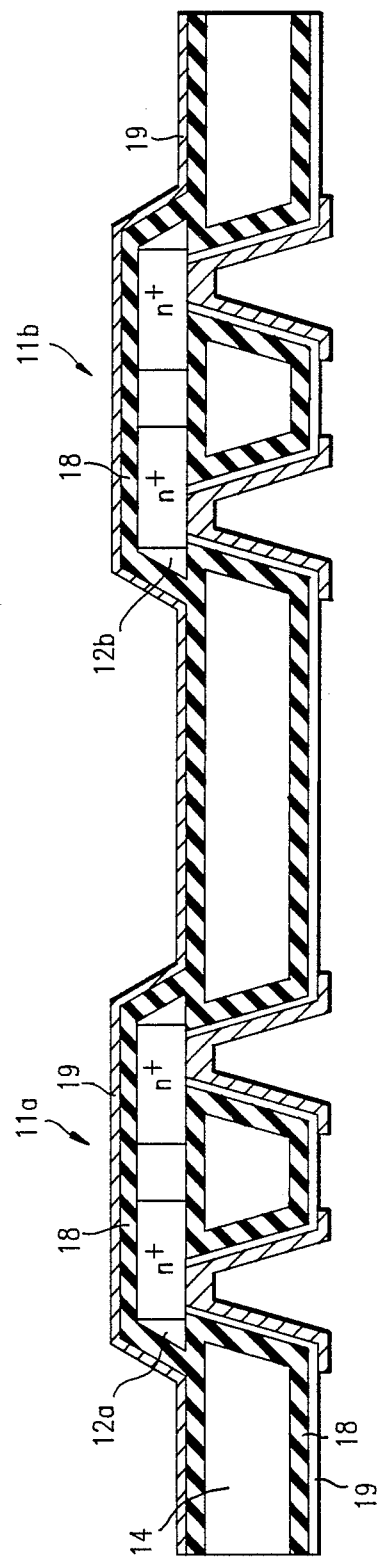
FIG. 4
FIG. 5

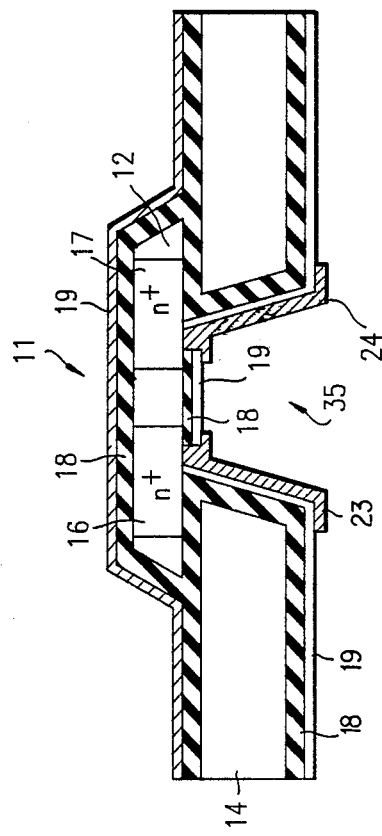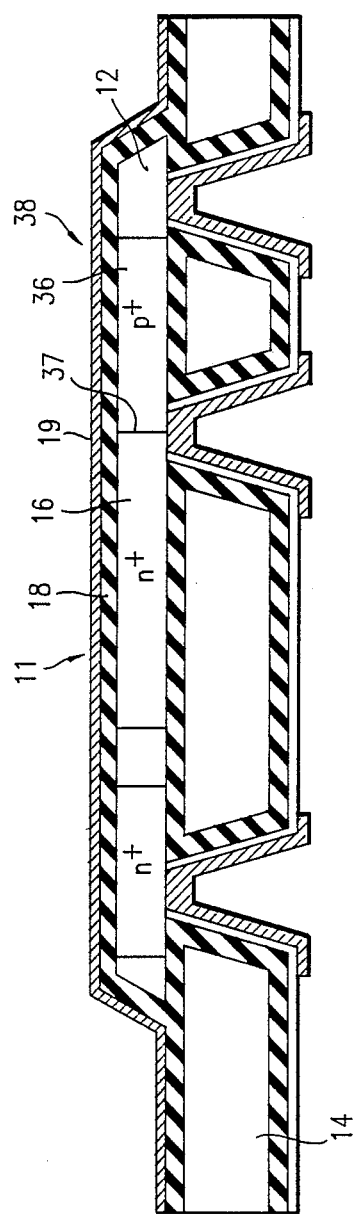

FIELD-EFFECT TRANSISTOR-TYPE SEMICONDUCTOR SENSOR

BACKGROUND OF THE INVENTION

1. Field of the Invention

This invention relates to a semiconductor sensor, and more particularly to a field-effect transistor-type sensor used for detecting the constituents of a solution.

2. Description of the Prior Art

In general, an ion-sensitive field-effect transistor (hereinafter, simply referred to as an ISFET) is known as an FET-type chemical sensor that detects the constituents of a solution. An ISFET comprises a source region and a drain region formed on a semiconductor substrate, and a gate portion having a gate-insulating film and a film sensitive to a specific ion of a solution. When the gate portion of the ISFET is immersed in a solution, the conductance between the source and drain regions changes in proportion to the ion concentration of specific constituents of the solution.

The ISFET detects the changes of such conductance and produces output signals corresponding to the ion concentration. Specifically, interface potentials are generated on the surface of the ion-sensitive film by the effect of a specific ion of the solution. Such interface potentials cause the conductance between the source and drain regions to change. This can be performed through the gate-insulating film.

As described above, at least the gate portion of an ISFET is immersed in a solution while in use. Thus, the ISFET must be protected from the penetration of the solution. Therefore, various configurations of electrical insulation have been considered to protect the electrodes and leads from deteriorating. For example, an ISFET that can securely protect its electrodes was disclosed by the inventor of the present invention.

FIG. 11 shows the configuration of the disclosed ISFET which employs a direct bonding-type semiconductor substrate. In FIG. 11, a first silicon substrate 41 and a second silicon substrate 42 are directly bonded to each other interposing an oxide film 43 therebetween. Such a direct-bonding configuration can be obtained in such a manner as follows. First, the surfaces of substrates to be bonded are polished to achieve a mirror finish. Next, a silicon oxide film is formed on at least one of the surfaces, and then the surfaces are cleaned. Thereafter, the surfaces of substrates are contacted to each other, and then are exposed to an atmosphere of a prescribed thermal processing. The first substrate 41 of the thus bonded substrates is etched by the use of a selective etching technique so as to form an island-shaped substrate. A source region 44 and a drain region 45 are formed in the island substrate 41. A P⁻-type channel region 46 is formed near the interface between the first and second substrates 41 and 42. A P⁺-type channel stopper layer 47 is formed adjoining the P⁻-type channel region 46.

The second substrate 42 is selectively etched so as to form an opening 48 at a position opposite to the channel region 46. Further, the bonded side of the first substrate 41 is partially exposed to the opening 48. A gate-insulating film 49 of silicon oxide and an ion-sensitive film 50 of silicon nitride are deposited on the exposed portion of the first substrate 41 and the walls of the opening 48. These constitute an ion-sensitive portion 51. The surfaces of bonded substates 41 and 42 are also coated with such films 49 and 50 for the purpose of water-resistance.

The source and drain electrodes 52 and 53 are formed on the surface of the first silicon substrate 41, respectively. However, the ion-sensitive film 50 of silicon nitride is not required on the side in proximity of the electrodes 52 and 53. Thus, other materials may also be used for water-resistance.

In this configuration, the ion-sensitive portion 51 is formed on one side of the first substrate 41, while the source and drain electrodes 52 and 53 are formed on the other side of the substrate 41. Thus, the electrodes 52 and 53 are not immersed in a solution, but only the sensitive portion 51 of the ISFET is immersed therein. Therefore, the ISFET is free from deterioration in terms of insulation characteristics caused by the penetration of a solution. Further, the ISFET can be manufactured by the use of planar processes.

However, the above-described ISFET still has many disadvantages including the following. Specifically, as shown in FIG. 11, the sensitive portion 51 is formed in a concave portion of the ISFET. Thus, the uniform thickness of the films 49 and 50 cannot be manufactured with consistent accuracy. Further, the ISFET is usually attached to a tube, and a solution to be measured flows through the tube. In this case, the concave portion 51 (i.e., the ion-sensitive portion) is immersed in the solution as described above. Thus, the solution can stagnate in the concave portion 51. Such stagnation prevents the efficient replacement of the solution with a fresh supply for subsequent measurement.

On the other hand, a technique for eliminating the above-described disadvantages has been disclosed. Specifically, according to such a technique, an ion-sensitive portion is not provided in a concave portion of the substrate, but in an island portion thereof. This means that the solution does not contact the concave portion, resulting in no stagnation of the solution. A uniform thickness of the ion-sensitive film and the gate-insulating film may also be formed. However, it is extremely difficult to embody an ISFET on the basis of such a technique because of the following reasons. In the technique, a thin film of silicon, which comprises the island portion, is formed on a quartz substrate. Source and drain regions are formed within the island portion. An ion-sensitive film is formed on the surface of the island portion through a gate-insulating film. Thus, two openings and two through holes must be made in the quartz substrate so as to form source and drain electrodes. However, it is extremely difficult to make holes in the quartz substrate which has strong corrosion resistance. It is theoretically possible to make holes in the quartz substrate if an etching process using hydrogen fluoride is performed for a long time of about 20 hours. Practically, masking materials, which can withstand such a long-time etching, are very hard to obtain. Above all, making a hole deeper as compared to an opening area involves great difficulties in terms of anisotropic etching.

Moreover, the disclosed technique claims that a monocrystalline silicon layer of 0.5 to 1 µm thick is formed on the quartz substrate. However, at present, forming a monocrystalline silicon layer on quartz, per se, is extremely difficult, and no experimental results on such formation have been located. Even if such a monocrystalline silicon layer is formed on a quartz substrate, the layer is only 0.5 to 1 µm thick. Thus, such a thin silicon layer can easily cause mechanical damage or undergo a peel-off phenomenon. In addition, quartz differs significantly from monocrystalline silicon in coefficient of thermal expansion. As a result, the thin monocrystalline silicon layer is subjected to higher stresses causing the layer to peel off.

SUMMARY OF THE INVENTION

Accordingly, one object of this invention is to provide a field-effect transistor-type semiconductor sensor having a configuration suitable for mass production and stable characteristics.

Briefly, in accordance with one aspect of this invention, there is provided a field-effect transistor-type semiconductor sensor which comprises a first semiconductor substrate, a second semiconductor substrate bonded directly to the first semiconductor substrate interposing an oxide film therebetween, a source region, a channel region and a drain region, each being provided in the first semiconductor substrate, a first insulating film provided on the surface of the first semiconductor substrate, a second insulating film deposited on the first insulating film, the second insulating film being sensitive to ion, and a plurality of openings provided in the second semiconductor substrate, the openings provided corresponding to the source and drain regions.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a cross-sectional view illustrating the first embodiment attached to a tube through which a solution to be measured flows;

FIG. 5 is a cross-sectional view illustrating a third embodiment according to the present invention;

FIG. 6 is a cross-sectional view illustrating a fourth embodiment according to the present invention;

FIG. 7 is a cross-sectional view illustrating a fifth embodiment according to the present invention;

DESCRIPTION OF THE PREFERRED EMBODIMENTS

Figure 1:
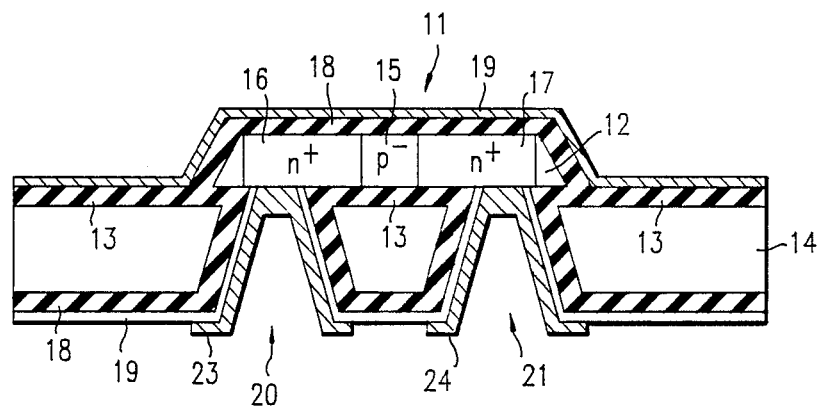
FIG. 1 is a cross-sectional view illustrating a first embodiment according to the present invention.

Referring now to the drawings, wherein like reference numerals designate identical or corresponding parts throughout the several views, and more particularly to FIG. 1 thereof, a first embodiment of this invention will be described.

In FIG. 1, a first $P^-$-type monocrystalline silicon substrate 12 of 12 $\mu$m thick is bonded through a silicon oxide 13 to a second monocrystalline silicon substrate 14 of 200 $\mu$m thick. The thickness of the first substrate 12 is required to be 10 $\mu$m at a minimum. This bonding is performed by use of the direct bonding technique which will be later described. As a result, the first and second substrates 12 and 14 are strongly bonded to each other interposing the silicon oxide film 13 therebetween. The first substrate 12 functions as an ion-sensitive portion 11 which will be described later in detail. A $P^-$-type channel region 15, an $n^+$-type source region 16 and an $n^+$-type drain region 17 are formed within the substrate 12. The first substrate 12 has a flat upper surface and inclined side surfaces. The entire peripheral surface of the substrate 12 is coated with a silicon oxide film 18 which serves as a gate-insulating film. A silicon nitride ($Si_3N_4$) film 19 sensitive to hydrogen ions is deposited on the silicon oxide film 18. The silicon nitride film 19 is deposited not only on the surface of the first substrate 12, but also on the silicon oxide film 18 on the surface of the second substrate 14.

The silicon nitride film 19 is sensitive to hydrogen ion, and also serves as a water-resistant protective film. Openings 20 and 21 are made in the second substrate 14, i.e., on opposite sides of the ion-sensitive portion 11. The average opening angles of the openings 20 and 21 are required to be in the range of 40° to 100°. The surfaces of the source and drain regions 16 and 17 are exposed to the openings 20 and 21. The silicon oxide film 18 and the silicon nitride film 19 are deposited on the surface of the second substrate 14 including the surface of the openings 20 and 21. Source electrode 23 and drain electrode 24, which are connected respectively to the source and drain regions 16 and 17, are formed in the openings 20 and 21.

In the above-described configuration of the semiconductor sensor, the first and second substrates 12 and 14 are strongly bonded to each other interposing the silicon oxide film 13. Namely, the first substrate 12 having a sufficient thickness of about 12 $\mu$m can be strongly bonded to the second substrate 14 by use of the direct bonding technique. Further, both the first and second substrates 12 and 14 are made of the same material, i.e., monocrystalline silicon. Thus, the coefficients of thermal expansion of both substrates are identical to each other. As a result, the first substrate 12 is free from adverse stresses. Further, the silicon oxide film 18 and the silicon oxide film 13 are both obtained by oxidizing monocrystalline silicon, i.e., the films 18 and 13 are identical to each other.

Thus, the entire surface of the first island-shaped silicon substrate including the bottom and side surfaces thereof is coated with the insulating film which is seamless and unified. As a result, the disadvantages of the conventional ISFET, such as leakage and peel-off phenomena, can be eliminated. Moreover, the silicon nitride film 19, which is sensitive to hydrogen ions and also serves as a water-resistant protective film, is deposited on the entire surface of the first and second substrates 12 and 14. Consequently, the penetration of a solution and the peel-off phenomena of the silicon oxide 18 can be effectively prevented.

Next, the processes of manufacturing the above-described first embodiment of this invention will be described with reference to FIGS. 2a through 2e.

Figure 2A:
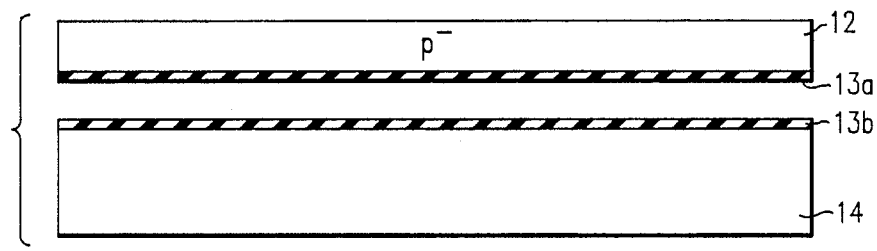
FIGS. 2a through 2e are cross-sectional views illustrating processes of manufacturing the first embodiment according to the present invention.

First, a first monocrystalline silicon substrate 12 and a second monocrystalline silicon substrate 14 are prepared. The surfaces of both the substrates 12 and 14 to be bonded are polished so as to achieve a mirror finish. The roughness of the thus polished surfaces is prescribed to 500 Å at a maximum, and preferably to 50 Å or less. Next, the substrates 12 and 14 are washed in a standard manner by the use of water, organic solvent, a mixed solution of hydrogen peroxide and sulfuric acid, boiling aqua regia (nitrohydrochloric acid), and hydrogen fluoride. Next, the thus mirror-finished surfaces of the substrates 12 and 14 are exposed to an atmosphere of high-temperature steam so as to achieve thermal oxidation. As a result, silicon oxide films 13a and 13b of about 1 $\mu$m thick are formed on the surfaces of the substrates 12 and 14. The first substrate 12 has a P$^-$-type conductivity and serves as a FET element-forming region (FIG. 2a).

Figure 2B:
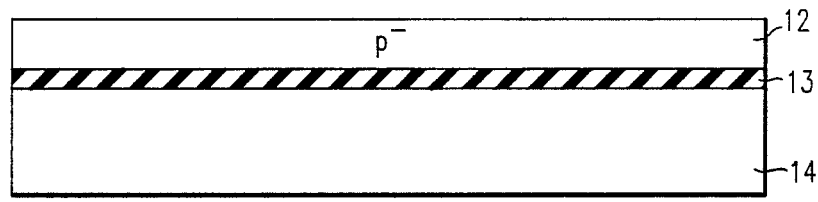

Thereafter, the substrates 12 and 14 are washed with water and organic solvent or the like. Further, the surfaces of the silicon oxide films 13a and 13b of the substrates 12 and 14 to be bonded are washed with pure deionizing water for a few minutes. Next, the substrates 12 and 14 are dehydrated at room temperatures by the use of a spinner. The object of this dehydrating process is to dehydrate excessive water leaving water adsorbed on the silicon oxide films 13a and 13b. Therefore, heat drying at 100° C. or more, which volatilizes substantially all of such adsorbed water, must be avoided. The water adsorbed on the silicon oxide films 13a and 13b forms a hydrophilic group (OH radical). Next, the substrates 12 and 14 are placed in close contact with each other in the clean atmosphere of Class 1 or better. Specifically, this process must be performed in a state in which substantially no foreign matter interposes between the silicon oxide films 13a and 13b. The thus contacted substrates 12 and 14 are exposed to an atmosphere of nitrogen at a temperature of 200° C. or more, and preferably of 1000° C. to 1200° C. In this atmosphere, prescribed thermal processes are performed so as to achieve the direct-bonding configuration having a bonding strength of 100 kg/cm$^2$ at a minimum. As a result, the substrates 12 and 14 are strongly bonded to each other interposing the silicon oxide film 13 (FIG. 2b). A P$^+$-type layer (not shown) may be previously formed on the bonded surface side of the first substrate 12. Such a layer serves as a channel stopper layer which stabilizes operation characteristics. The impurity concentration of such a P$^+$-type layer must be lower than that of the n$^+$-type layers of source and drain regions which will be later formed.

Figure 2C:
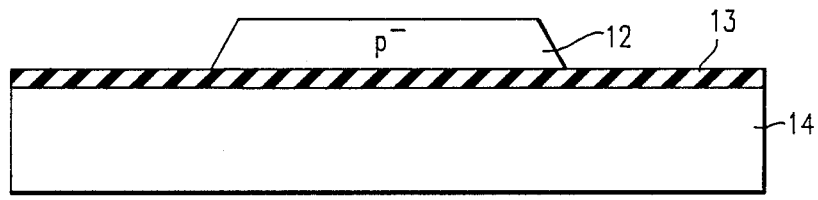

Next, the thus bonded first and second substrates 12 and 14 are respectively machined so as to achieve prescribed thickness, i.e., about 12 $\mu$m for the first substrate 12, and about 200 $\mu$m for the second substate 14. Thereafter, the first substrate 12 is selectively etched by the use of a mixed etchant of hydrogen fluoride, nitric acid and acetic acid. As a result, the first substrate 12 is formed into an island-shape (FIG. 2c).

Figure 2D:
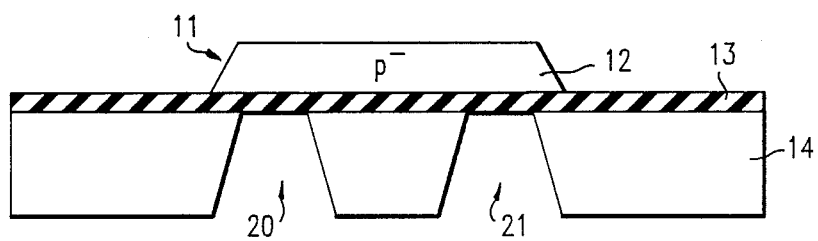

Next, the second substrate 14 is selectively etched by use of an anisotropic etching technique with a mixed etchant of ethylenediamine, pyrocatechol and water. As a result, openings 20 and 21 are formed, which reach the silicon oxide film 13 of the bonded portion of the first and second substrates 12 and 14 (FIG. 2d). Thereafter, the bonded substrates 12 and 14 are exposed to an atmosphere of thermal processing so as to form an oxide film 26 on the entire surface thereof. Next, the oxide film 26 on the surface of the first substrate 12 is selectively etched so as to form windows 27 and 28. Thereafter, n-type impurities are implanted through such windows 27 and 28 into the first substrate 12 by the use of an ion implantation technique.

Figure 2E:
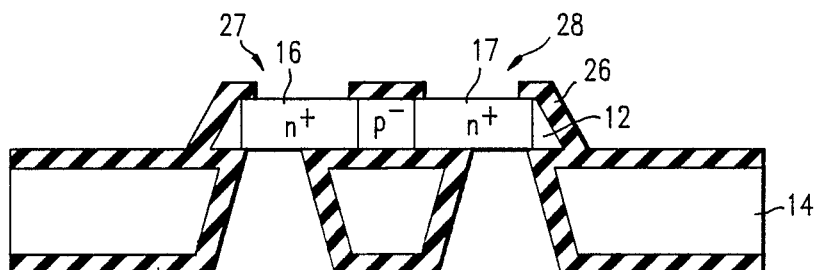

As a result, an n$^+$-type source region 16 and an n$^+$-type drain region 17 are formed in the first substrate 12. The source and drain regions 16 and 17 are formed so deep as to reach the bonded interface (FIG. 2e). When the source and drain regions 16 and 17 are formed, the diffusion therefor can be performed not only from the upper side, but also from the lower side of the first substrate 12. This causes the diffusion length thereof to be halved. Next, the oxide film 26 of FIG. 2e is once eliminated, and again a thermal oxidation process is performed. Thus, a silicon oxide film 18 is formed on the entire surface of the substrates 12 and 14, as shown in FIG. 1.

Further, a silicon nitride film 19 is formed on the thus formed silicon oxide film 18. The film 19 serves not only as a hydrogen ion-sensitive film, but also as a water-resistant protective film. In FIG. 1, two contact holes are made in the openings 20 and 21 at portions opposite to the bonded interface of the first and second substrates 12 and 14. Thereafter, a source electrode 24 and a drain electrode 25 are formed respectively on the surfaces of the openings 20 and 21. The electrodes 24 and 25 are securely contacted respectively to the source and drain regions 16 and 17. A region, which is sandwiched between the source and drain regions 16 and 17, serves as a gate region 15. As a result, an ISFET in the first embodiment according to the present invention is completed.

Figure 3:
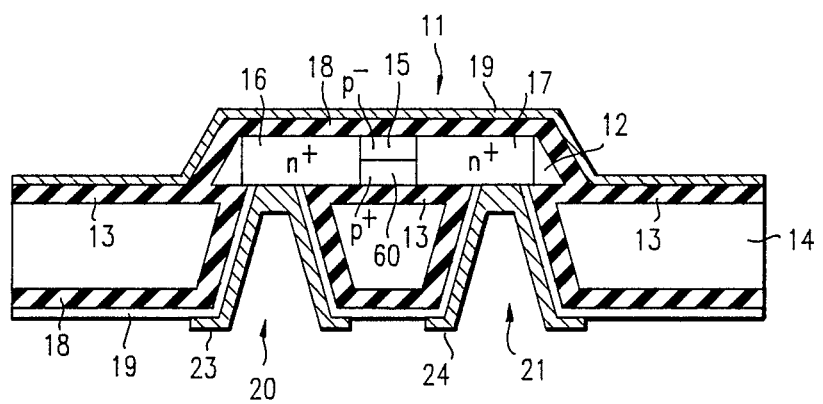
FIG. 3 is a cross-sectional view illustrating a second embodiment according to the present invention.

FIG. 3 shows a second embodiment according to the present invention. In this embodiment, a P$^+$ channel stopper region 60 is formed in a channel region 15 at a position adjoining the oxide film 13 of the second substrate 14.

FIG. 4 shows a state in which the ISFET of the first embodiment (FIG. 1) is attached to a tube 29 through which a solution to be measured flows. As shown in FIG. 3, ISFET is inserted into a hole 30 of the tube 29 and fixed by the use of bonding resin 31. In this case, the sensitive portion 11, which is the first substrate 12 of FIGS. 1 and 2, is disposed at the inside of the tube 29. Next, leads 32 and 33 are connected respectively to source and drain electrodes 23 and 24. Thereafter, they are all coated with protective mold resin 34 as shown in FIG. 3.

As described above, the sensitive portion 11 is isolated from the source and drain electrodes 23 and 24 because the electrodes 23 and 24 are formed on both sides of the bonded substrates (i.e., dielectric solution configuration). Thus, only the sensitive portion 11 can be immersed in a solution. As a result, satisfactory insulation characteristics between the sensitive portion 11 and the electrodes 23 and 24 can be securely maintained. In addition, the sensitive portion 11 is formed on the flat surface. Thus, the uniform thickness of the gate-insulating film 18 and the sensitive film 19 can be easily obtained. Moreover, the stagnation of a solution in the sensitive portion 11 can be avoided because of its flat surface. Therefore, when various solutions are measured in the state of FIG. 4, the replacement of such solutions can be rapidly performed.

Further, in the sensor of this invention, the uniformity of the silicon oxide film and the silicon nitride film and covering the entire surface of the substrate with such films have been achieved. Moreover, the degree of freedom in designing the thickness of the silicon substrate that constitutes the ISFET has been expanded. In addition, the residual stress of the silicon substrate has been eliminated. As a result, the mechanical strength of the ISFET has been enhanced. Therefore, even when the ISFET is immersed in a solution under pressure, the substrate that constitutes ISFET can be prevented from peel-off phenomena. The ISFET can also be prevented from the penetration of the solution. Consequently, the reliability of measurements and the work efficiency of measuring procedures can be significantly enhanced.

The ISFET of this embodiment has the pH sensitivity of about 53 mv/pH in the range of pH 3 to pH 11. In the case when the solutions of pH 9 and pH 4 were repeatedly measured on experiment, stable outputs were obtained for more than three months.

Moreover, a sensor was manufactured using a film made of PVC (polyvinyl chloride) into which nitrone nitrate is dispersed. Specifically, such a film is formed on the entire surface of the substrate that constitutes the sensor. It was confirmed that the sensor maintained stable operation without any peel-off phenomena of the sensitive film even after the use for a month. This means that the sensor has improved reliability as compared to a sensor in which a sensitive film is formed only on its gate portion. It was also confirmed that when the thickness of the first substrate was 10 μm or more, the peel-off resistance thereof was further enhanced. This fact proved that the sufficient thickness of a sensitive film and covering the entire surface of the substrate with such a film were significantly effective in preventing the peel-off phenomenon of an organic-sensitive film, which was one of the essential factors in determining the life of the ISFET.

FIG. 5 shows a third embodiment according to the present invention. In this embodiment, a multi-ISFET configuration is formed as follows. Specifically, a first substrate is selectively etched so as to form two island-shaped regions 12a and 12b. In each of island regions 12a and 12b, an ISFET of the same configuration as that of FIG. 1 is formed. The region 12a constitutes a sensitive portion 11a, and the region 12b constitutes a sensitive portion 11b. Each of the sensitive portions 11a and 11b functions independently.

As described above, the use of the bonded substrates of dielectric isolation configuration can easily achieve the intergration of plural ISFETs isolated from each other. Thus, the isolation between the respective ISFETs is securely maintained. As a result, a multiple chemical sensor can be obtained, which has plural sensitive portions constituted by different sensitive films. Such sensitive portions have individual characteristics, and are free from interacting with each other. For example, two different sensitive films were prepared. Specifically one sensitive film included nitrone nitrate for use in detecting nitrate ion. The other sensitive film included quaternary ammonium salt for use in detecting ammonium ion. These sensitive films were based on a matrix made of polyvinyl chloride (PVC). The thus prepared sensitive films were used to constitute two sensitive portions. Two ISFETs with these sensitive portions were actually used to measure solutions. The measurements were made using a silver-silver chloride electrode as a reference electrode. As a result, close agreement was obtained between the outputs of these measurements and the outputs in the case of single ISFET.

FIG. 6 shows a fourth embodiment which differs from the ISFET of FIG. 1 in that only one opening 35 is provided. The opening 35 has source and drain electrodes 23 and 24 on its sidewalls. This embodiment has the same advantages as those of the first embodiment of FIG. 1.

FIG. 7 shows a fifth embodiment according to the present invention. In FIG. 7, a temperature-compensating diode 37 is incorporated in a sensitive portion 11. Specifically, a $P^+$-type layer 36 is formed adjoining an $n^+$ source region 16. As a result, an interface, which is between the $P^+$-type layer 36 and the $n^+$ source region 16, constitutes the temperature-compensating diode 37.

Figure 8:
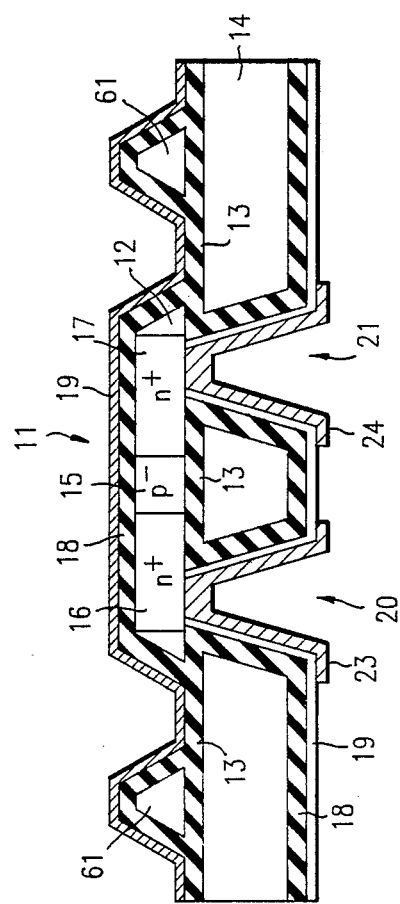
FIG. 8 is a cross-sectional view illustrating a sixth embodiment according to the present invention.

FIG. 8 shows a sixth embodiment according to the present invention. In this embodiment, a semiconductor protrusion 61 is formed on a second semiconductor substrate 14 at a position surrounding a sensitive portion 11. When the periphery of this ISFET is coated with mold resin, the protrusion 61 protects the sensitive portion 11 from being covered with such mold resin. The protrusion 61 can be formed at the same time as a first semiconductor substrate 12 is island-shaped.

Figure 9:
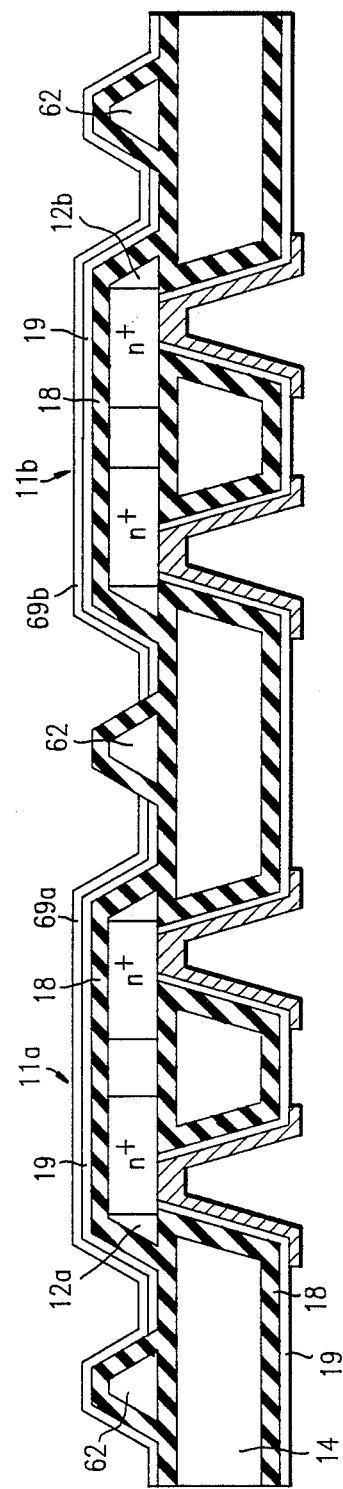
FIG. 9 is a cross-sectional view illustrating a seventh embodiment according to the present invention.

FIG. 9 shows a seventh embodiment according to the present invention. In this embodiment, a semiconductor protrusion 62 is formed on a second semiconductor substrate 14 at a position surrounding sensitive portions 11a and 11b. The protrusion 62 protects the sensitive portions 11a and 11b from being covered with mold resin in the same manner as in the sixth embodiment. Further, different sensitive films 69a and 69b, which can detect different constituents, can be provided in the sensitive portions 11a and 11b. Specifically, the sensitive films 69a and 69b can be securely isolated from each other by the protrusion 62. Moreover, in the process of forming the sensitive film on the substrate, the liquid material of the sensitive film is apt to spread out to the portions which must be protected from such spread. The protrusion 62 in this embodiment prevents such undesirable spread-out of the liquid material. The films 69a and 69b are selected from an ion sensitive film, an enzyme or microorganism selective film, or a gas permeable film.

Figure 10:
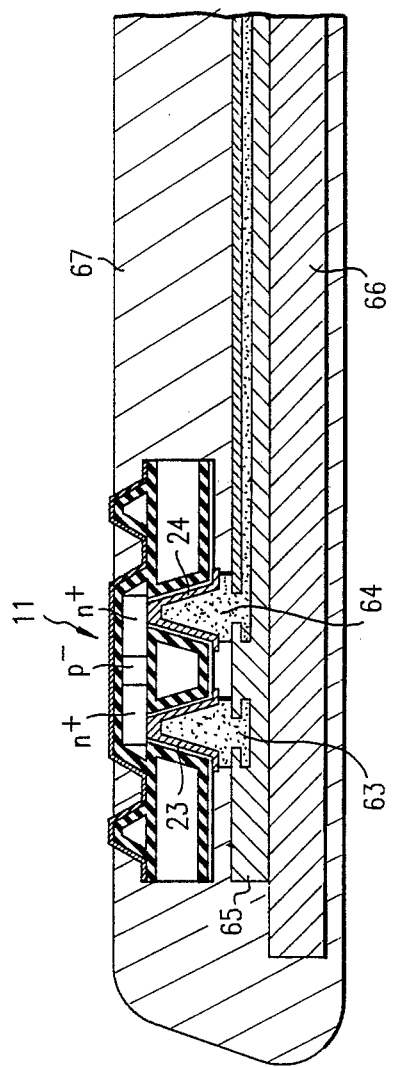
FIG. 10 is a cross-sectional view illustrating an eighth embodiment according to the present invention.
Figure 11:
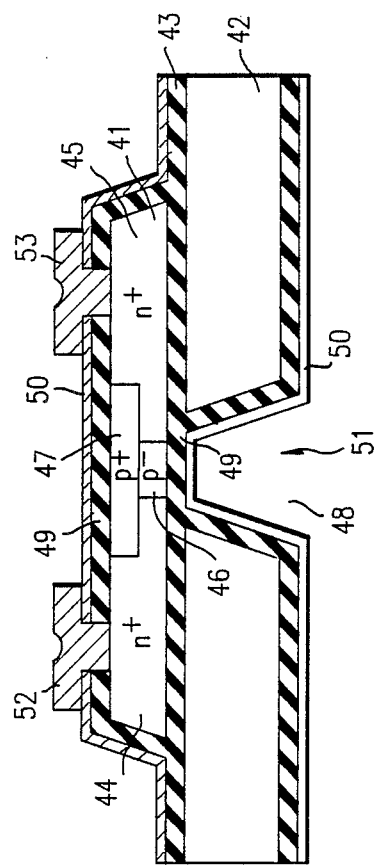
FIG. 11 is a cross-sectional view illustrating a conventional semiconductor sensor.

FIG. 10 shows an eighth embodiment according to the present invention. In this embodiment, the ISFET of FIG. 8 is incorporated in a measuring probe. Specifically, source and drain electrodes 23 and 24 are electrically connected to corresponding pads on a printed circuit board 65 by conductive members 63 and 64. The printed circuit board 65 is securely supported by a reinforcing board 66. The entire periphery of the ISFET and the boards 65 and 66 excepting the surface of a sensitive portion 11 are molded with epoxy resin 67. The probe of this embodiment can directly touch an object to be measured such as a plant leaf, for example, so as to detect the constituents thereof.

Moreover, not only such a simple element as the temperature-compensating diode 37 of the fifth embodiment, but also more sophisticated components such as multiplexers and microprocessors, can be incorporated in the ISFET.

In addition, a film of $Al_2O_3$ or a film of $Ta_2O_3$, which has satisfactory protective functions and sensitive characteristics, can be formed as a substitute for a film of $Si_3N_4$. The film of $Al_2O_3$ or the film of $Ta_2O_3$ can also be formed on the film of $Si_3N_4$ resulting in a double layer.

Obviously, numerous additional modifications and variations of the present invention are possible in light of the above teachings. It is therefore to be understood that within the scope of the appended claim, the invention may be practiced otherwise than as specifically described herein.

What is claimed is:

1. A field-effect transistor-type semiconductor sensor comprising:
    a first semiconductor substrate;
    a second semiconductor substrate bonded directly to said first semiconductor substrate interposing an oxide film therebetween;
    a source region, a channel region and a drain region, each being provided in said first semiconductor substrate;
    a first insulating film on said first semiconductor substrate;
    a second insulating film on said first insulating film, said second insulating film being sensitive to a specified ion; and
    a source electrode and a drain electrode, each being connected to a corresponding one of said source and drain regions through said second semiconductor substrate.

2. The sensor of claim 1, wherein said first and second semiconductor substrates include monocrystalline silicon.

3. The sensor of claim 1, wherein said first insulating film includes a silicon oxide film, and said second insulating film includes a silicon nitride film, a tantalum oxide film and an aluminum oxide film.

4. The sensor of claim 1, wherein said first semiconductor substrate is formed as an island.

5. The sensor of claim 4, further comprising first and second insulating films covering the periphery of the sensor.

6. The sensor of claim 4, further comprising first and second insulating films formed on the surface of said island-shaped semiconductor substrate, said films extending to the surface of said second semiconductor substrate.

7. The sensor of claim 4, including a plurality of island-shaped semiconductor substrates bonded to said second semiconductor substrate.

8. The sensor of claim 7, further comprising first and second insulating films covering the periphery of the sensor.

9. The sensor of claim 7, further comprising first and second insulating films formed on the surface of said plural island-shaped first semiconductor substrates, said films extending to the surface of said second semiconductor substrate.

10. The sensor of claim 9, further comprising the film being sensitive covering on the second insulating film.

11. The sensor of claim 10, the film includes an ion sensitive film, an enzyme or microorganism selective sensitive film, or a gas permeable film.

12. The sensor of claim 7, further comprising a semiconductor protrusion provided on said second semiconductor substrate, said protrusion surrounding said plural first island-shaped semiconductor substrates.

13. The sensor of claim 12, further comprising a film being a sensitive covering on the second insulating film.

14. The sensor of claim 13, the film includes an ion sensitive film, an enzyme or microorganism selective sensitive film, or a gas permeable film.

15. The sensor of claim 13, the film covers on the sensor are inside of the semiconductor protrusion.

16. The sensor of claim 4, further comprising a semiconductor protrusion provided on said second semiconductor substrate, said protrusion surrounding said first island-shaped semiconductor substrate.

17. The sensor of claim 1, further comprising two openings in the second substrate, one opening having a source electrode therein and the other opening having a drain electrode therein, each electrode being connected to a corresponding one of said source and drain regions.

18. The sensor of claim 1, further comprising a single opening in the second substrate having both source and drain electrodes therein, each electrode being connected to a corresponding one of said source and drain regions.

19. The sensor of claim 1, further comprising a temperature-compensating diode in said first semiconductor substrate at a position adjoining one of said source region and said drain region.

20. The sensor of claim 1, wherein said first semiconductor substrate has a thickness of 10 $\mu$m at a minimum.

21. The sensor of claim 1, wherein said channel region includes a channel stopper region provided at a position adjoining the oxide film on said second semiconductor substrate, said channel stopper region having the same conductivity-type as that of said channel region, and having a higher impurity concentration than said channel region.

22. The sensor of claim 1, further comprising a semiconductor protrusion provided on said second semiconductor substrate, said protrusion surrounding said first semiconductor substrate.

23. The sensor of claim 1, further comprising an insulating member for incorporating the sensor, said insulating member exposing only the ion-sensitive insulating film.

24. The sensor of claim 23, wherein said insulating member is made of resin.

25. The sensor of claim 24, wherein said resin includes epoxy resin.

26. The sensor of claim 1, further comprising a film being a sensitive covering on the second insulating film.

27. The sensor of claim 26, the film includes an ion sensitive film, an enzyme or microorganism selective sensitive film, or a gas permeable film.

28. A field-effect transistor-type semiconductor sensor comprising:
    a first semiconductor substrate;
    a second semiconductor substrate bonded directly to said first semiconductor substrate interposing an oxide film therebetween;
    a source region, a channel region and a drain region, each being provided in said first semiconductor substrate;
    a first insulating film on said first semiconductor substrate;
    a second insulating film on said first insulating film, said second insulating film being sensitive to a specified ion; and
    a source electrode and a drain electrode, each being connected to a corresponding one of said source and drain regions;
    wherein there are two openings in the second substrate, one opening having a source electrode therein and the other opening having a drain electrode therein, each electrode being connected to a corresponding one of said source and drain regions.

29. A field-effect transistor-type semiconductor sensor comprising:
    a first semiconductor substrate;
    a second semiconductor substrate bonded directly to said first semiconductor substrate interposing an oxide film therebetween;

a source region, a channel region and a drain region, each being provided in said first semiconductor substrate;

a first insulating film on said first semiconductor substrate;

a second insulating film on said first insulating film, said second insulating film being sensitive to a specified ion; and a source electrode and a drain electrode, each being connected to a corresponding one of said source and drain regions;

wherein a single opening in the second substrate having both source and drain electrodes therein, each electrode being connected to a corresponding one of said source and drain regions.

30. A field-effect transistor-type semiconductor sensor comprising:

a first semiconductor substrate;

a second semiconductor substrate bonded directly to said first semiconductor substrate interposing an oxide film therebetween;

a source region, a channel region and a drain region, each being provided in said first semiconductor substrate;

a first insulating film on said first semiconductor substrate;

a second insulating film on said first insulating film, said second insulating film being sensitive to a specified ion; and a source electrode and a drain electrode, each being connected to a corresponding one of said source and drain regions;

wherein a temperature-compensating diode in said first semiconductor substrate at a position adjoining one of said source region and said drain region.

* * * * *